United States Patent [19]

Fritz

[11] Patent Number: 4,525,144
[45] Date of Patent: Jun. 25, 1985

[54] DENTAL ATTACHMENT

[76] Inventor: Bobby D. Fritz, 801-D Osler Dr., Jonesboro, Ariz. 72401

[21] Appl. No.: 522,462

[22] Filed: Aug. 11, 1983

[51] Int. Cl.³ .............................................. A61C 1/07
[52] U.S. Cl. .................................. 433/118; 433/129; 433/144
[58] Field of Search ............... 433/118, 119, 129, 122, 433/123, 124, 125, 126, 127, 147, 165, 166, 143, 144; 279/42, 43, 48, 99, 52; 30/336; 51/595 S

[56] References Cited

U.S. PATENT DOCUMENTS

| | | | |
|---|---|---|---|
| 351,153 | 10/1886 | Bigby | 433/129 |
| 1,316,685 | 9/1919 | Cates | 433/123 |
| 2,507,872 | 5/1950 | Unsinger | 30/336 |
| 3,086,288 | 4/1963 | Balamuth et al. | 433/119 |
| 3,731,385 | 5/1973 | Farber et al. | 279/52 |
| 3,843,143 | 10/1974 | Laxson | 279/99 |
| 4,330,278 | 5/1982 | Martin | 433/86 |

Primary Examiner—John J. Wilson
Attorney, Agent, or Firm—Walker & McKenzie

[57] ABSTRACT

An attachment component is provided to allow a vibratory-type dental tool to use low cost, disposable surgical blades. The attachment component includes a collet member having a slot into which the shank of the blade is inserted and a sleeve member for being attached to the handle of the dental tool and having a cavity for receiving the collet member to cause the blade to be wedged within the slot.

1 Claim, 16 Drawing Figures

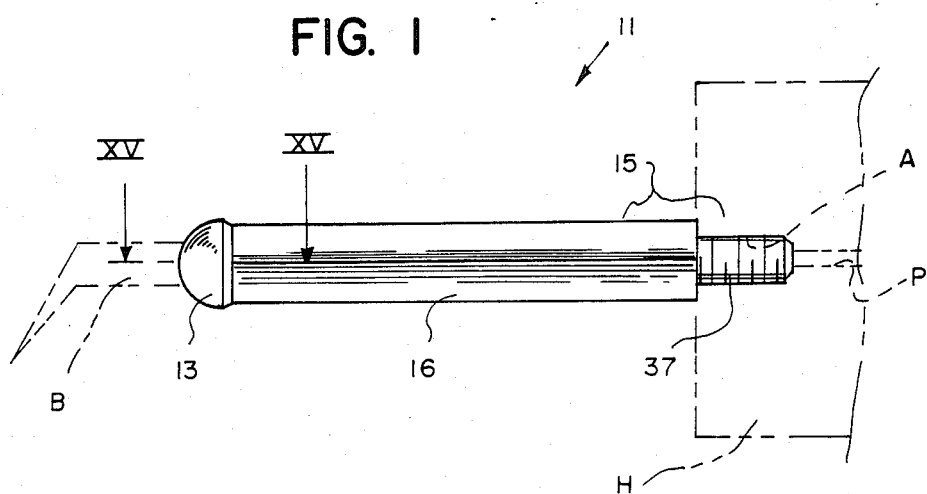
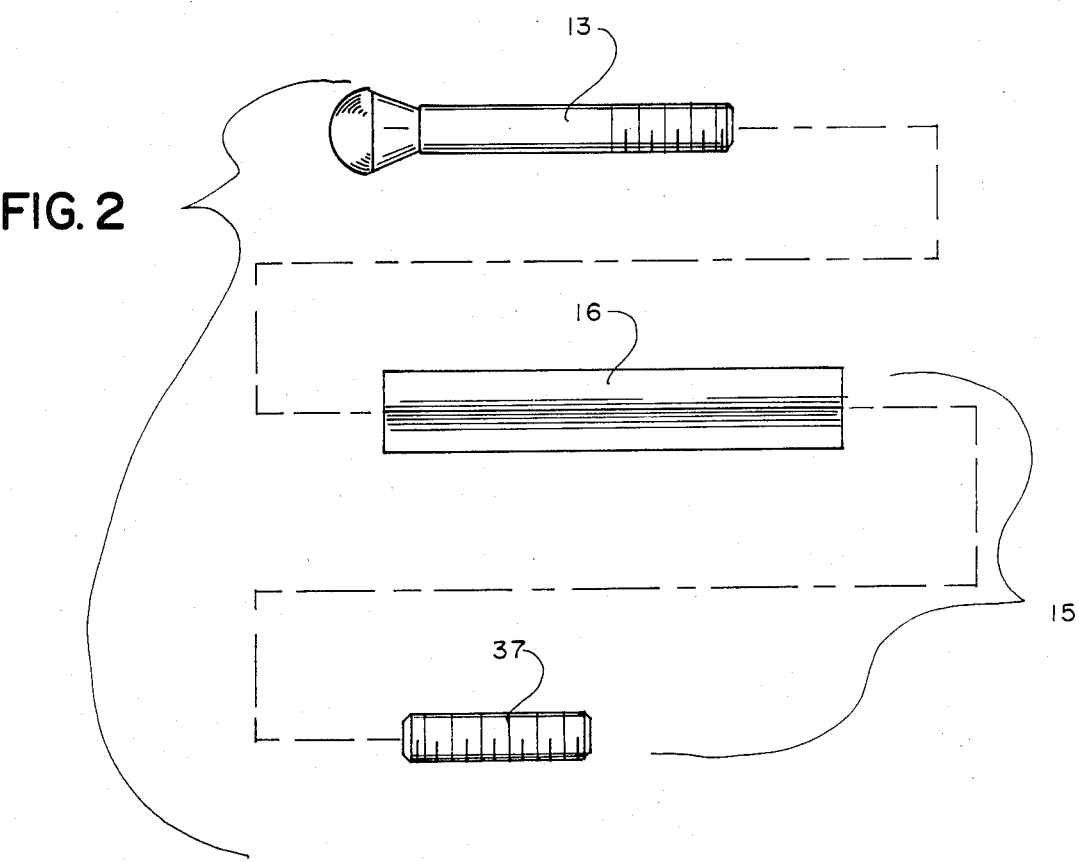

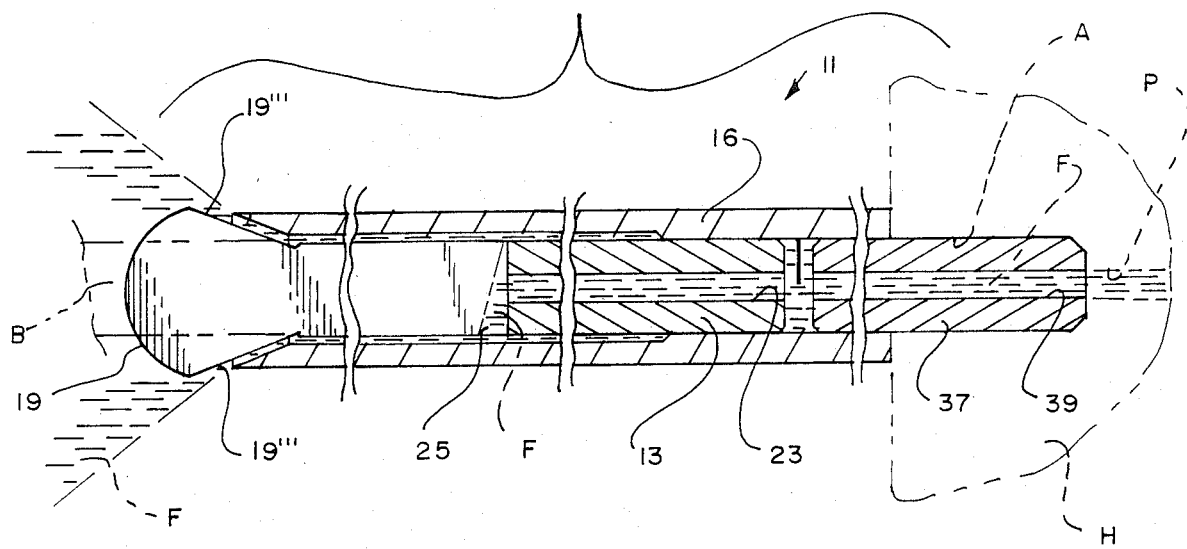

DENTAL ATTACHMENT

BACKGROUND OF THE INVENTION

1. Field of the Invention

The present invention relates to an attachment means for attaching a low cost, disposable surgical cutting blade to a hand-held vibratory dental instrument.

2. Description of the Prior Art

Various patents have been issued for ultrasonic and vibratory surgical cutting instruments used in dentistry. See, for example, the following U.S. Patents: U.S. Pat. No. 4,249,901 granted to Wieser; U.S. Pat. No. Re. 30,536 granted to Perdreaux, Jr.; U.S. Pat. No. 3,995,372 granted to Rapuano; U.S. Pat. No. 3,763,411 granted to Goof; U.S. Pat. No. 3,133,351 granted to Seggern; U.S. Pat. No. 3,526,219 granted to Balamuth; U.S. Pat. No. 2,714,890 granted to Vang; U.S. Pat. No. 2,990,616 granted to Balamuth; U.S. Pat. No. 3,086,288 granted to Balamuth. None of the above patents disclose or suggest the present invention.

SUMMARY OF THE INVENTION

The concept of the present invention is to provide the user (a dentist or surgeon) of a hand-held vibratory instrument with a means of coupling a low cost, disposable surgical blade thereto.

Therefore, a common disadvantage of all known prior devices is that the knife blade or tool blit and the means for attaching such knife blade or tool bit to the vibratory instrument are constructed as a one-piece, integral unit so that when the knife blade or tool bit becomes dull or damaged, one would have to discard the entire unit. See, for example, Balamuth U.S. Pat. Nos. 2,990,616 and 3,086,288 which disclose various arrangements of knife blades and tool bits. Thus, when replacing the knife blade or tool bit, it would be very expensive to the user.

An object of the present invention is to provide an attachment that when the knife blade becomes dull or damaged, only the knife blade would be replaced.

Another object of the present invention is that the attachment may be used on most vibratory dental instruments.

The attachment means of the present invention includes, in general, a collet member that receives the cutting blade and a sleeve member that receives the collet member and that is securable to a vibratory dental instrument.

BRIEF DESCRIPTION OF THE DRAWINGS

FIG. 1 is a side elevational view of the attachment means of the present invention with the surgical blade and vibratory instrument shown in phantom lines.

FIG. 2 is an exploded view of the present invention.

FIG. 13 is a side elevational view of the threaded portion of the present invention showing aperture in hidden lines.

FIG. 14 is a front elevational view of the threaded portion of the present invention, the rear elevational view being exactly the same thereof.

FIG. 15 is an enlarged sectional view substantially as taken on line XV—XV of FIG. 1, the shank portion of blade shown in phantom lines.

FIG. 16 is an enlarged sectional view of the attachment means showing the fluid traveling through the attachment, a portion of the surgical blade and vibratory handle shown in phantom lines.

DESCRIPTION OF THE PREFERRED EMBODIMENT

Figure 3:
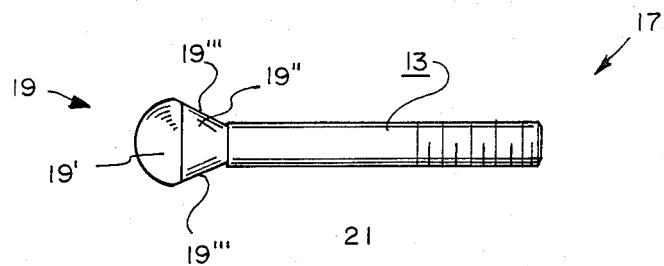
FIG. 3 is a side elevational view of the collet member of the present invention.

The attachment means 11 of the present invention consists, in general, of a collet chuck including a collet member 13 and a sleeve member 15.

The attachment means 11 of the present invention is used as a means for securing a disposable surgical blade B to the hand-held handle H of a vibratory instrument. The vibratory instrument may be of various constructions now used in dental and surgical work and well-known to those skilled in the art. Preferably, the vibratory instrument is a hand-held air delivery-type vibratory instrument such as the "Titan-S" sonic scaler produced by Syntex Dental Products, Inc. of Valley Forge, PA 19482. Such a vibratory instrument may be adapted in various ways to receive a knife blade or tool bit unit such as by way of the threaded aperture A in the handle H (see FIGS. 1 and 16). Such a vibratory instrument is preferably provided with a fluid passageway P and with means for allowing fluid F, such as water, to be sprayed therethrough (see FIGS. 1 and 16) for reasons well-known to those skilled in the art.

The disposable surgical blade B used with the present invention preferably has a substantially flat shank portion S. Such disposable surgical blades B are commonly available and are now manufactured by, for example, the Beaver Surgical Instrument Company.

The collet member 13 is preferably constructed out of a stainless steel rod, being a material acceptable to medical methods of sterilization. The collet member 13 has a bolt-like appearance consisting of a first end 17, a second end 19 and a body 21, connecting the two ends thereof. The first end 17 is externally threaded, starting at the first end 17 running up approximately one-third of the entire length of the collet member 13. The first end 17 also has an aperture 23 drilled in the center of the first end 17 to be used as a fluid or water channel. The aperture 23 runs parallel with the external thread on the first end 17.

Figure 4:
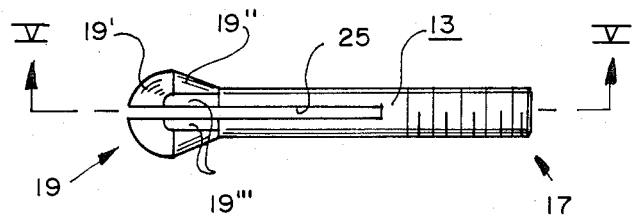
FIG. 4 is a top plan view of the collet member thereof.
Figure 5:
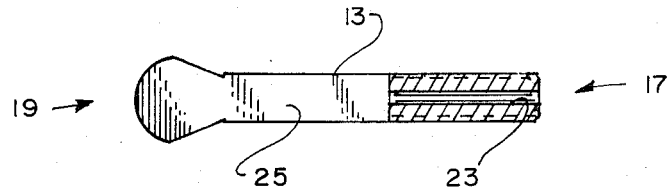
FIG. 5 is a sectional view substantially as taken on line V—V of FIG. 4.
Figure 6:
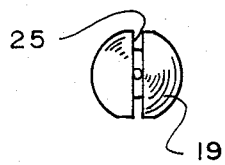
FIG. 6 is a front elevational view of the collet member of the present invention.
Figure 7:
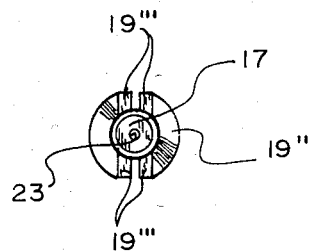
FIG. 7 is a rear elevational view of the collet member of the present invention.
Figure 8:
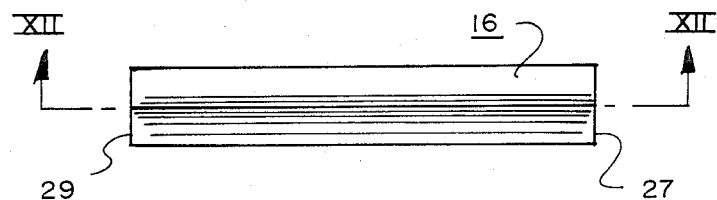
FIG. 8 is a side elevational view of the sleeve member of the present invention.
Figure 9:
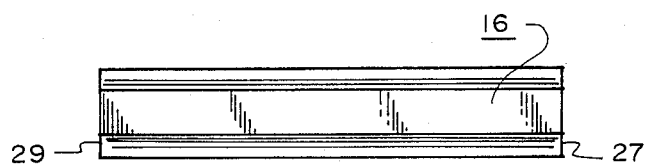
FIG. 9 is a top plan view of FIG. 8.
Figure 10:
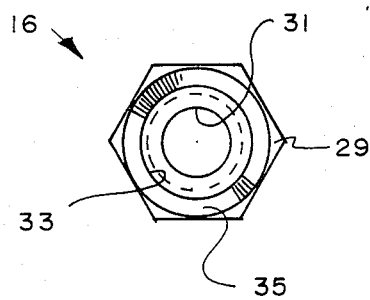
FIG. 10 is an enlarged front elevational view of the sleeve member of the present invention.
Figure 11:
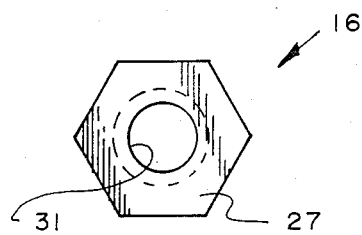
FIG. 11 is an enlarged rear view at the sleeve member of the present invention.

The second end 19 of the collet member 13 has an expanded end 19' being of a convex or one-half of a sphere-like in appearance and an outward flared 19" portion connecting the expanded end 19' to the bolt-like body 21 and of the second end 19 of the collet member 13 (see FIG. 4). The second end 19 of the collet member 13 has a slot 25 starting from the extreme second end 19 going toward the first end 17 of approximately two-thirds of the length thereof. The slot 25 has a width wide enough to accomodate the flat shank portion S of the surgical blade B. Please note in FIGS. 4 and 5 that the top and bottom of the outward flare 19″ and a portion of the convex surface 19′, there is a flat machined portion 19‴. The machined portion 19‴ serves as a fluid or water outlet.

Figure 12:
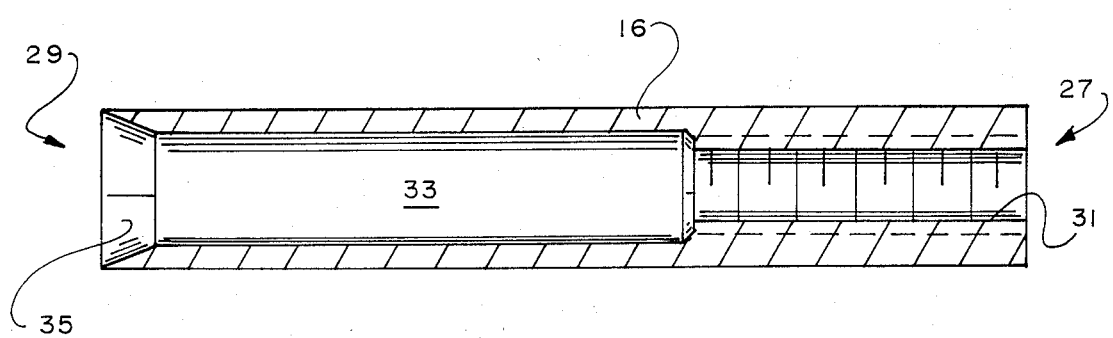
FIG. 12 is an enlarged sectional view substantially as taken on line XII—XII of FIG. 8.

The sleeve member 15 of the present invention preferably includes a sleeve 16 which may be constructed out of an oblong, hexagon shaped stainless steel stock or the like. The sleeve 16 has a first end 27 and a second end 29. The first end 27 has a threaded aperture 31. The length thereof would be long enough to receive a portion of the first end 17 of the collet member 13 and a portion of the threaded portion 37. The second end 29 of the sleeve 16 contains a smooth cavity 33, extending approximately two-thirds of the length thereof. The second end 29 also has an outwardly flared portion 35 on the extreme outside edge of the cavity 33, shown best in FIG. 12.

The outward flare 35 of the sleeve 16 and the outward flare 19″ of the collet member 13 coact with one another (as shown in FIG. 15). The first end 17 of the collet member 13 is inserted into the cavity 33 of the sleeve 16 and screwed in the threaded aperture 31, thus pulling the outward flare 19″ of the expanded end 19 into the cavity 33 of the sleeve 16. Therefore, the outward flare 19″ and the outward flare 35 would have a wedging effect on each other, thus forcing the slot 25 of the collet member 13 to apply an inward pressure shown by arrows 41 against the flat shank S of the blade member B.

The sleeve member 15 of the present invention preferably includes an externally threaded portion 37 for allowing the sleeve member 15 to be screwed into the threaded aperture A of the handle H of the vibratory instrument. The threaded portion may be integrally constructed with the sleeve 16 or may be a separate component. Thus, the threaded portion 37 may be constructed out of a stainless steel rod with threads running the entire length thereof for being screwed part way into the threaded aperture 31 in the first end 27 of the sleeve 16 (see FIG. 16). An aperture 39 may be provided lengthwise through the threaded portion 37 substantially along the longitudinal axis thereof to provide a fluid or water passageway threthrough. The aperture 39 may be drilled or otherwise formed in the threaded portion 37. On certain models of vibratory instruments, the threaded portion 37 may be threaded into the aperture A in the handle H of the vibratory instrument as shown in FIG. 1 or the handle intself may have a threaded appendix. Thus, the sleeve 16 would be attached directly to the threaded appendix (threaded appendix not shown) by way of the threaded aperture 31. Various other specific methods of attaching the sleeve 16 to the handle H of the vibratory instrument may be used as will be apparent to those skilled in the art.

In FIG. 16 the assembled collet chuck 11 shows the passageway of the fluid F through the collet chuck 11 and out of the water outlets 19‴. Please note the fluid F flows around the body 21 at the collet member 13.

As thus constructed, the present invention provides an attachment that can be easily attached to a vibratory instrument and that allows low cost, disposable surgical blades to be used. The water spray irrigates and cleanses the incision.

Although the present invention has been described and illustrated with respect to the preferred embodiment therefor, it is not to be so limited since changes and modifications can be made therein which are within the full intended scope of the invention.

I claim:

1. A dental surgical tool comprising:
   (a) an air delivery-type vibratory instrument including a hand-held handle having a fluid passageway therethrough, said handle having a threaded aperture therein;
   (b) a cutting blade having a substantially flat shank portion; and
   (c) attachment means for attaching said blade to said handle of said vibratory instrument, said attachment means including a collet member having a first end and a second end, said second end of said collet member having a slot receiving said shank portion of said blade, at least a portion of the outer surface of said second end of said collet member flaring outwardly away from said first end, at least a portion of the outer surface of said first end of said collet member being threaded, said attachment means including a sleeve member having a first end and a second end, at least a portion of said first end of said sleeve member being threaded and being received in said threaded aperture of said handle of said vibrating instrument, said second end of said sleeve member having a threaded cavity receiving the threaded portion of said first end of said collet member to cause said blade to be wedged within said slot in said collet member.

* * * * *

UNITED STATES PATENT AND TRADEMARK OFFICE
CERTIFICATE OF CORRECTION

PATENT NO. : 4,525,144
DATED : June 25, 1985
INVENTOR(S) : Bobby D. Fritz

It is certified that error appears in the above-identified patent and that said Letters Patent is hereby corrected as shown below:

On the title page, Item [76] "Ariz." should read --AR--.

Signed and Sealed this

Twenty-second Day of April 1986

[SEAL]

Attest:

DONALD J. QUIGG

Attesting Officer   Commissioner of Patents and Trademarks